United States Patent [19]

Iwane et al.

[11] Patent Number: 5,543,547
[45] Date of Patent: Aug. 6, 1996

[54] METHOD OF PRODUCING AROMATIC CARBONATE

[75] Inventors: Hiroshi Iwane; Hidekazu Miyagi; Satoshi Imada; Shoichi Seo; Takahiro Yoneyama, all of Inashiki-gun, Japan

[73] Assignee: Mitsubishi Chemical Corporation, Tokyo, Japan

[21] Appl. No.: 384,258

[22] Filed: Feb. 3, 1995

Related U.S. Application Data

[63] Continuation of Ser. No. 160,145, Dec. 2, 1993, abandoned.

[30] Foreign Application Priority Data

Mar. 8, 1993 [JP] Japan .................................. 5-046740
Jun. 28, 1993 [JP] Japan .................................. 5-157216

[51] Int. Cl.$^6$ .......................................................... C07C 69/96
[52] U.S. Cl. ........................................... 558/274; 558/270
[58] Field of Search ........................................ 558/274, 270

[56] References Cited

U.S. PATENT DOCUMENTS

| | | | |
|---|---|---|---|
| 4,201,721 | 5/1980 | Hallgren | 558/270 |
| 5,132,447 | 7/1992 | King, Jr. | 558/270 |
| 5,142,086 | 8/1992 | King, Jr. et al. | 558/274 |

*Primary Examiner*—Paul J. Killos
*Assistant Examiner*—Dwayne C. Jones
*Attorney, Agent, or Firm*—P.C. Oblon, Spivak, McClelland, Maier & Neustadt

[57] ABSTRACT

The present invention relates to a method of producing an aromatic carbonate by reacting an aromatic hydroxy compound, carbon monoxide and oxygen using as a catalyst a specified catalyst system containing palladium and cerium compounds. Specifically, the present invention relates to a method of producing an aromatic carbonate by reacting an aromatic hydroxy compound, carbon monoxide and oxygen in the presence of a catalyst containing the following compounds:

(A) at least one selected from palladium and palladium compounds;

(B) at least one of trivalent or tetravalent cerium compounds;

(C) at least one selected from quaternary ammonium salts and quaternary phosphonium salts;

(D) at least one selected from quinones and reduction products thereof, i.e., aromatic diols; or (A) and (B) components of the above; and (E) at least one inorganic halide selected from alkali metal halides and alkali earth metal halides.

15 Claims, No Drawings

METHOD OF PRODUCING AROMATIC CARBONATE

This application is a continuation of application Ser. No. 08/160,145, filed on Dec. 2, 1993, now abandoned.

BACKGROUND OF THE INVENTION

1. Field of the Invention

The present invention relates to a method of producing an aromatic carbonate from an aromatic hydroxy compound, carbon monoxide and oxygen using a specified catalyst system. An aromatic carbonate, particularly diphenyl carbonate is useful as a raw material for polycarbonate or the like.

2. Description of the Related Art

A method of reacting an aromatic hydroxy compound with phosgene is generally used for producing an aromatic carbonate. However, this method has many problems as an industrial production method because of the high toxicity of phosgene and the by-production of large amounts of inorganic salts.

Some methods have thus been proposed which do not use phosgene in which an aromatic carbonate is produced from an aromatic hydroxy compound, carbon monoxide and oxygen.

Japanese Patent Publication No. 56-38144 discloses a method which uses as a catalyst a palladium compound, a compound containing a metal from the groups IIIA, IVA, VA, VIA, IB, IIB, VIB or VIIB in the periodic table, and a base. Japanese Patent Publication No. 56-38145 discloses a method which uses a palladium compound, a manganese or cobalt complex, a base and a desiccating agent. Japanese Patent Laid-Open No. 1-165551 discloses a method which uses a palladium compound, iodine and zeolite. Japanese Patent Laid-Open No. 2-104564 discloses a method which uses a palladium compound, a bivalent or trivalent manganese compound, tetraalkylammonium halide and quinone. Japanese Patent Laid-Open No. 2-142754 discloses a palladium compound, a bivalent or trivalent cobalt compound, tetraalkylammonium halide and quinone. Japanese Patent Laid-Open No. 5-25095 discloses a method which uses a palladium compound, a cobalt compound, an organic or inorganic halide and a basic compound.

Japanese Patent Laid-Open No. 5-58961 discloses a method which uses a palladium compound, a cobalt compound and an alkali metal halide.

Japanese Patent Laid-Open No. 5-97775 (U.S. Pat. No. 5,142,086 and European Patent Laid-Open No. 507,546-A2) discloses a method which uses a catalyst system comprising (a) a palladium compound; (b) a quaternary ammonium salt; (c) an inorganic compound as a cocatalyst selected from cobalt, iron, cerium, manganese, molybdenum, samarium, vanadium chromium and copper compounds; (d) an organic cocatalyst selected from aromatic ketones, aliphatic ketones, and aromatic polycyclic coal tar hydrocarbons.

However, thee methods have critical problems concerning the low activity of the catalyst used, and the low yield of an aromatic carbonate based on the starting aromatic hydroxy compound, and re thus unsatisfactory as industrial production methods. Tis is supposedly due to the phenomena where the activity of the catalyst used is decreased by the water produced by reaction, and that hydrolysis o an aromatic carbonate is accelerated in the conventional catalyst system. The methods proposed for preventing this phenomena include a method of using a large amount of coexisting dehydrating agent or removing the water produced (Japanese Patent Laid-Open No. 54-135744) and a method of distilling off the produced water by reaction distillation (Japanese Patent Laid-Open No. 4-261142). However, it could not be said that these methods have sufficient effects.

The conventional methods also have the problem that large amounts of by-products, particularly phenoxyphenols which cannot be easily separated from an intended product, are produced by oxidation of an aromatic hydroxy compound.

SUMMARY OF THE INVENTION

It is an object of the present invention to solve the various problems of conventional methods of producing aromatic carbonates from aromatic hydroxy compounds, carbon monoxide and oxygen, and provide a method of producing an intended aromatic carbonate with high yield and high selectivity.

The inventors found that the yield of an aromatic carbonate can be improved by using as a catalyst the specific catalyst system below containing palladium and cerium compounds. The present invention provides an industrial method of producing an aromatic carbonate which permits the production of an aromatic carbonate with high yield while maintaining high catalytic activity without using a large amount of dehydrating agent or installing a specific apparatus.

The present invention provides a method of producing an aromatic carbonate by reacting an aromatic hydroxy compound, carbon monoxide and oxygen, wherein the reaction is effected in the presence of a catalyst consisting of the following compounds:

(A) at least one selected from palladium and palladium compounds;

(B) at least one of trivalent or tetravalent cerium compounds;

(C) at least one selected from quaternary ammonium salts and quaternary phosphonium salts; and (D) at least one selected from quinones and reduction products thereof, i.e., aromatic diols; or (A) at least one selected from palladium and palladium compounds;

(B) at least one of trivalent or tetravalent cerium compounds; and (E) at least one inorganic halide selected from alkali metal halides and alkali earth metal halides.

DETAILED DESCRIPTION OF THE INVENTION

1. Raw Material (1) Aromatic hydroxy compound

The aromatic hydroxy compound used in the present invention is an aromatic mono- or poly-hydroxy compound. Examples of such hydroxy compounds include phenol: substituted phenols such as p-cresol, 2,6-xylenol, 2,4,6-trimethylphenol, 2,3,4,5-tetramethylphenol, ethylphenol, propylphenol, methoxyphenol, ethoxyphenol, chlorophenol, 2,4-dichlorophenol, bromophenol, 2,4-dibromophenol and position isomers thereof; naphthol; substituted naphthols such as 2-methylnaphthol, 2-ethylnaphthol, 2-chloronaphthol, 2-bromonaphthol and position isomers thereof; bisphenols such as 2,2-bis(4-hydroxyphenyl)propane and position isomers thereof; various biphenols such as 4,4-biphenol and position isomers thereof; various heteroaromatic hydroxy compounds such as 4-hydroxypyridine and position isomers thereof; and alkyl or halogen substitution products of the above compounds. Of these compounds, phenol is preferred.

(2) Carbon monoxide

The carbon monoxide used in the present invention may be high-purity carbon monoxide or carbon monoxide diluted with another gas such as nitrogen, argon, carbon dioxide or hydrogen, which have no bad effects on the reaction.

(3) Oxygen

The oxygen used in the present invention may be high-purity oxygen, air or oxygen diluted with another gas such as nitrogen, argon, carbon dioxide or hydrogen, which have no bad effects on the reaction.

2. Catalyst (A) Palladium or palladium compound

Examples of palladium or palladium compounds that can be used in the present invention include palladium black; palladium/carbon, palladium/alumina, palladium/silica and the like in which palladium is supported on porous carriers; inorganic palladium salts such as palladium chloride, palladium bromide, palladium iodide, palladium sulfate, palladium nitrate and the like; organic palladium salts such as palladium acetate, palladium oxalate. Further, palladium (II) acetylacetonate, a palladium complex compound such as $PdCl_2(PhCN)_2$, $PdCl_2 (PPh_3)_2$, $Pd(CO) (PPh_3)_3$, $[Pd(NH_3)_4] Cl_2$, $Pd(C_2H_4) (PPh_3)_2$ or the like in which carbon monoxide, nitrile, amine, phosphine or olefin is co-ordinated around palladium, or a mixture of palladium and a compound which produces the above complex compound in the reaction system can also be used.

Although a large amount of palladium component may be used in the reaction without any problems, the molar ratio of the palladium component to the aromatic hydroxy compound is preferably within the range of $10^{-5}$ to 1, more preferably $10^{-4}$ to $10^{-1}$.

(B) Trivalent or tetravalent cerium compound

Examples of trivalent or tetravalent cerium compounds that can be used in the present invention include cerium/carbon, cerium/alumina, cerium/silica and the like in which cerium is supported on porous carriers; inorganic salts such as cerium chloride, cerium bromide, cerium sulfate, cerium nitrate and the like; organic salts such as cerium acetate, cerium oxalate and the like. Also cerium acetylacetonate, a cerium complex compound in which carbon monoxide, a nitrile, an amine, a phosphine or an olefin is co-ordinated around cerium, or a mixture of cerium and a compound which produces the above complex compound in the reaction system may be used.

When cerium is supported on a porous carrier, cerium and palladium may, of course, be supported on the same porous carrier.

Although the cerium component can be used in any desired ratio to the palladium component, the molar ratio of the cerium component to the palladium component is preferably within the range of $10^{-2}$ to $10^2$, more preferably $10^{-1}$ to 10.

(C) Quaternary ammonium salt or quaternary phosphonium salt (quaternary onium salt)

The quaternary onium salt used in the present invention is a compound expressed by the formula, $R^1R^2R^3R^4NX$ or $R^1R^2R^3R^4PX$, wherein $R^1$ through $R^4$ are each an alkyl group having 1 to 8 carbon atoms, an aryl group having 6 to 12 carbon atoms, and the groups $R^1$ through $R^4$ may be either the same or different. Examples of the groups $R^1$ through $R^4$ through $R^4$ include methyl, ethyl, propyl, butyl, pentyl, hexyl, octyl, cyclohexyl, phenyl tolyl, xylyl and naphthyl groups. X is an anion such as a hydroxy group, a halogen anion such as a chloride anion, a bromide anion, an iodide anion or the like; an organic anion such as a phenoxide anion, an acetate anion or the like. Of these anions, a bromide anion is preferred. A chloride anion has low activity, and an iodide anion causes much combustion of carbon monoxide Preferred examples of bromides include tetra-n-ethylammonium bromide, tetra-n-butylammonium bromide and tetraphenylphosphonium bomide.

The molar ratio of the quaternary onium salt to the palladium component (A) used in reaction is preferably within the range of $10^{-1}$ to $10^3$, more preferably 1 to $10^2$, and most preferably 50 or less. Although the molar ratio of the quaternary onium salt to the aromatic hydroxy compound is not limited, the molar ratio is preferably within the range of $10^{-4}$ to $10^{-1}$, more preferably $10^{-3}$ to $10^{-2}$.

(D) Quinones and reduction products thereof, i.e., aromatic diols

Examples of quinones or reduction products thereof, i.e., aromatic diols, that can be used in the present invention include 1,4-benzoquinone, 1,2-benzoquinone, catechol, naphthoquinone, anthraquinone, hydroquinone and the like. Of these compounds, 1,4-benzoquinone and hydroquinone are preferred.

The amount of the quinone or reduction product thereof used in the present invention is not limited. However, if the amount is excessively small, the yield and selectivity are decreased due to an increase in amount of the oxidation by-products, and if the amount is excessively large, the reaction is inhibited by the quinone or aromatic diol.

The molar ratio of the compound to the palladium component (A) is preferably within the range of $10^{-1}$ to $10^3$, more preferably 1 to $10^2$, and most preferably 40 or less. The molar ratio of the compound to the aromatic hydroxy compound is preferably within the range of $10^{-4}$ to $10^{-1}$, more preferably $10^{-3}$ to $10^{-2}$.

(E) Inorganic halide

The inorganic halide used in the present invention is an alkali metal or alkali earth metal halide. A chloride and a bromide are preferred as such halides. Specifically, cesium chloride, sodium bromide, potassium bromide, rubidium bromide, cesium bromide, and barium bromide are preferred. Although the amount of the inorganic halide used in the reaction is not limited, the molar ratio of the halide to the palladium component (A) is preferably within the range of $10^{-2}$ to $10^3$, more preferably $10^{-1}$ to $10^2$.

3. Reaction Method and Reaction Condition

Reaction is effected in a reactor in which the aromatic hydroxy compound and the catalyst comprising the components (A), (B), (C) and (D) or the components (A), (B) and (E) are charged under heating conditions and pressures of carbon monoxide and oxygen.

The reaction pre;sure is within the range of $10^{-1}$ to 500 $Kg/cm^2$, preferably 1 to 250 $Kg/cm^2$.

The molar ratio of each of carbon monoxide and oxygen to the hydroxy compound is within the range of $10^{-2}$ to 50, preferably $10^1$ to 10.

Although any desired ratio may be selected as the composition ratio between carbon monoxide and oxygen, the composition ratio is preferably beyond the combustion range of these gases from the viewpoint of safety. It is also effective to dilute these gases with an inert gas having no effect on the reaction. If the amount of the diluent gas is excessively large, the partial pressures of carbon monoxide and oxygen are undesirably decreased.

The composition of the reaction gases cannot be determined unconditionally because the combustion range depends upon the temperature, pressure and the type of the diluent gas used. Generally, carbon monoxide is used in excess, and the partial pressures of oxygen is 1 to 10% and dilution gas used is 0 to 50%, respectively, of the total pressure. When the reaction gases become short of any one of the gas components due to the reaction proceeds, the gas component may be supplied under pressure at each time of shortage, or a gas mixture having a constant composition may be continuously supplied to the reactor under pressure.

The reaction temperature is 20° to 300° C., preferably 60° to 250° C., and more preferably 80° to 130° C. Although the reaction time depends upon reaction conditions, the reaction time is generally several minutes to several hours.

In reaction, an inert solvent such as hexane, heptane, cyclohexane, benzene, toluene, xylene, methylene chloride, chloroform, chlorobenzene, diethyl ether, diphenyl ether, tetrahydrofuran, dioxane, ethyl acetate, methyl formate, acetonitrile can be used. When the aromatic hydroxy compound as a raw material is used as a reaction solvent, another solvent need not be used.

After reaction, the high-purity aromatic carbonate produced can be isolated and purified from the reaction mixture without any other treatment or after the solid is separated by filtration, by a purification method such as distillation purification or crystallization. The catalyst components obtained from the filtration or distillation residue can be recovered and then used again for the next reaction.

When the catalyst is recovered and used again, it is preferable to use a catalyst system comprising the components (A), (B) and (E) rather than a catalyst system comprising the components (A), (B), (C) and (D) because the former system does not contain a quaternary ammonium salt or quaternary phosphonium salt (quaternary onium salt) as a component, and thus exhibits relatively higher thermal stability.

EXAMPLES

The present invention is described in detail below with reference to examples and comparative examples.

Example 1

3.3 g (35 mmol) of phenol, 26.0 mg (0.012 mmol Pd) of 5%-palladium/carbon, 4.0 mg (0.012 mmol) of cerium (III) acetate monohydrate, 82 mg (0.26 mmol) of tetra-n-butylammonium bromide and 13 mg (0.12 mmol) of hydroquinone were charged in a 30-ml Hastelloy autoclave. After air in the system was replaced by carbon monoxide, 60 Kg/cm$^2$ of carbon monoxide and 30 Kg/cm$^2$ of dry air were introduced into the autoclave, followed by reaction at 100° for 1 hour. As a result of gas chromatoraphic analysis of the reaction solution, the yield of diphenyl carbonate was 17% (3.0 mmol).

When reaction was further continued for 2 hours, diphenyl carbonate was obtained with a yield of 25.8% (4.5 mmol). The yields of phenyl salicylate and p-phenoxyphenol which were produced as by-products were 0.55% (0.095 mmol) and 0.20% (0.034 mmol), respectively. The selectivity of p-phenoxyphenol was 0.7%.

Example 2

The same operation as that in Example 1 was performed using 3.1 g (33 mmol) of phenol, 25.5 mg (0.012 mmol Pd) of 5%-palladium/carbon, 4.0 mg (0.012 mmol) of cerium (III) acetate monohydrate, 101 mg (0.24 mmol) of tetraphenylphosphonium bromide and 13 mg (0.12 mmol) of hydroquinone. After reaction for 3 hours, diphenyl carbonate was obtained with a yield of 23.7% (3.9 mmol). Phenyl salicylate and p-phenoxyphenol were produced as by-products with yields of 0.55% (0.090 mmol) and 0.15% (0.025 mmol), respectively. The selectivity of p-phenoxyphenol was 0.6%.

Comparative Example 1

The same operation as that in Example 1 was performed using 3.1 g (33 mmol) of phenol, 25.6 mg (0.012 mmol Pd) of 5%-palladium/carbon, 4.3 mg (0.012 mmol) of manganese (III) acetylacetonate, 80 mg (0.25 mmol) of tetra-n-butylammonium bromide and 13 mg (0.12 mmol) of hydroquinone. After reaction for 1 hour, diphenyl carbonate was obtained with a yield of 10% (1.6 mmol).

When reaction was further continued for 2 hours, the yield of diphenyl carbonate was 6.7% (1.1 mmol). The yields of phenyl salicylate and p-phenoxyphenol, which were by-products, were 0.19% (0.031 mmol) and 0.25% (0.041 mmol), respectively. The selectivity of p-phenoxyphenol was 3.5%.

Example 3

The same operation as that in Example 1 was performed using 4.5 g (49 mmol) of phenol, 12.7 mg (0.006 mmol Pd) of 5%-palladium/carbon, 2.0 mg (0.006 mmol) of cerium (III) acetate monohydrate, 127 mg (0.40 mmol) of tetra-n-butylammonium bromide and 21 mg (0.19 mmol) of hydroquinone. After reaction for 3 hours, diphenyl carbonate was obtained with a yield of 12.6% (3.0 mmol). Phenyl salicylate and p-phenoxyphenol were produced as by-products with yields of 0.30% (0.073 mmol) and 0.18% (0.044 mmol), respectively. The selectivity of p-phenoxyphenol was 1.4%.

Comparative Example 2

The same operation as that in Example 3 was performed using 4.5 g (48 mmol) of phenol, 3.0 mg (0.006 mmol Pd) of 5%-palladium/carbon, 2.1 mg (0.006 mmol) of cerium (III) acetate monohydrate and 121 mg (0.38 mmol) of tetra-n-butylammonium bromide. After reaction for 3 hours, diphenyl carbonate was obtained with a yield of 7.4% (1.8 mmol). Phenyl salicylate and p-henoxyphenol were produced as by-products with yields of 0.21% (0.05 mmol) and 0.38% (0.09 mmol), respectively. The selectivity of p-phenoxyphenol was 4.7%.

Example 4

3.0 g (32 mmol) of phenol, 25.8 mg (0.012 mmol Pd) of 5%-palladium/carbon, 4.2 mg (0.012 mmol) of cerium (III) acetate monohydrate, and 5.18 mg (0.24 mmol) of cesium bromide were charged in a 30-ml Hastelloy autoclave. After air in the system was replaced by carbon monoxide, 60 Kg/cm$^2$ of carbon monoxide and 30 Kg/cm$^2$ of dry air were introduced into the autoclave, followed by reaction at 100° C. for 3 hours. As a result of gas chromatographic analysis of the reaction solution, the yield of diphenyl carbonate was 9.4% (1.5 mmol). The yields of phenyl salicylate and p-phenoxyphenol which were produced as by-products were 0.32% (0.05 mmol) and 0.13% (0.02 mmol), respectively. After the completion of reaction, the gas phase contained 0.4% of carbon dioxide.

Examples 5 to 9

The same reaction as that in Example 4 was effected except that each of the various halides were used in place of cesium bromide. The halides used, the amounts thereof and the yields of diphenyl carbonate are shown in Table 1.

TABLE 1

| Example No. | Halide (mg) | Yield of diphenyl carbonate (%) |
| --- | --- | --- |
| 5 | CsCl (41) | 8.4 |
| 6 | NaBr (26) | 5.0 |
| 7 | KBr (29) | 5.6 |
| 8 | RbBr (40) | 8.7 |
| 9 | $BaBr_2 \cdot 2H_2O$ (81) | 4.1 |

Comparative Example 3

The same operation as that in Example 4 was performed using 3.0 g (32 mmol) of phenol, 25.6 mg (0.012 mmol Pd) of 5%-palladium/carbon, 3.0 mg (0.012 mmol) of cobalt (II) acetate tetrahydrate, and 51.4 mg (0.24 mmol) of cesium bromide. As a result, diphenyl carbonate was obtained with a yield of 1.5% (0.24 mmol). After the completion of reaction, the gas phase contained 0.3% of carbon dioxide.

Comparative Example 4

The same operation as that in Example 4 was performed using 3.0 g (32 mmol) of phenol, 25.8 mg (0.012 mmol Pd) of 5%-palladium/carbon, 4.2 mg (0.012 mmol) of cerium (III) acetate monohydrate, and 62.7 mg (0.24 mmol) of cesium iodide. As a result, diphenyl carbonate was obtained with a yield of 0.8% (0.12 mol). After the completion of reaction, the gas phase contained 10.6% of carbon dioxide.

Example 10

12.0 g (128 mmol) of phenol, 101 mg (0.048 mmol Pd) of 5%-palladium/carbon, 16 mg (0.048 mmol) of cerium (III) acetate monohydrate, and 165 mg (0.98 mmol) of cesium chloride were charged in a 50-ml astelloy autoclave. After air in the system was replaced by carbon monoxide, 60 $Kg/cm^2$ of carbon monoxide and 30 $Kg/cm^2$ of dry air were introduced into the autoclave, followed by reaction at 100° for 3 hours. As a result, the yield of diphenyl carbonate was 7.3% (4.7 mmol). After the reaction solution was transferred to a 50-ml flask, the solution was heated to 50° C. under reduced pressure to distill off phenol, and was further heated to 150° C. to distill off diphenyl carbonate. The residual catalyst was put in an autoclave, and 11.4 g (121 mmol) of phenol was added thereto. After air in the system was replaced by carbon monoxide, 60 $Kg/cm^2$ of carbon monoxide and 30 $Kg/cm^2$ of dry air was introduced into the autoclave, followed by reaction at 100° C. for 3 hours. As a result, diphenyl carbonate was obtained with a yield of 6.8% (4.1 mmol).

What is claimed is:

1. A method of producing an aromatic carbonate by reacting an aromatic hydroxy compound, carbon monoxide and oxygen, wherein reaction is effected under pressure within the range of 0.1 to 500 $Kg/cm^2$ at a temperature of 20° to 300° C., in a reaction system in the presence of the following compounds:

(A) at least one member selected from the group consisting of palladium and palladium compounds;

(B) at least one trivalent or tetravalent cerium compound;

(C) at least one member selected from the group consisting of quaternary ammonium salts and quaternary phosphonium salts; and (D) at least one member selected from the group consisting of quinones and reduction products thereof, the molar ratio of component (A) to the aromatic hydroxy compound being within the range of $10^{-5}:1$ to 1:1 and a molar ratio of the component (B) to the component (A) being within the range $10^{-2}:1$ to $10^2:1$.

2. A method according to claim 1, wherein the molar ratio of the component (A) to the aromatic hydroxy compound is within the range of $10^{-4}:1$ to $10^{-1}:1$.

3. A method according to claim 1, wherein the molar ratio of the component (B) to the component (A) is within the range of $10^{-1}:1$ to 10:1.

4. A method according to claim 1, wherein the reaction pressure is within the range of 1 to 250 $Kg/cm^2$.

5. A method according to claim 1, wherein the reaction temperature is within the range of 60° to 250° C.

6. A method according to claim 1, wherein said quaternary ammonium salts are quaternary ammonium halides and said quaternary phosphonium salts are quaternary phosphonium halides.

7. A method according to claim 1, wherein the molar ratio of the component (C) to the component (A) is within the range of $10^{-1}:1$ to $10^2:1$, and the molar ratio of the component (D) to the component (A) is within the range of $10^{-1}:1$ to $10^3:1$.

8. A method according to claim 7, wherein the molar ratio of the component (C) to the component (A) is from $10^{-1}:1$ to 50:1, and the molar ratio of the component (D) to the component (A) is from $10^{-1}:1$ to 40:1.

9. A method of producing an aromatic carbonate by reacting an aromatic hydroxy compound, carbon monoxide and oxygen, wherein reaction is effected under pressure within the range of 0.1 to 500 $Kg/cm^2$ at temperature of 20° to 300° C., in a reaction system in the presence of the following compounds:

(A) at least one member selected from the group consisting of palladium and palladium compounds;

(B) at least one trivalent or tetravalent cerium compound; and (E) at least one inorganic halide selected from the group consisting of alkali metal chlorides and bromides and alkali earth metal chlorides and bromides, the molar ratio of component (A) to the aromatic hydroxy compound being within the range of $10^{-5}:1$ to 1:1 and a molar ratio of the component (B) to the component (A) being within the range of $10^{-2}:1$ to $10^2:1$.

10. A method according to claim 9, wherein the molar ratio of the component (A) to the aromatic hydroxy compound is within the range of $10^{-4}:1$ to $10^-:1$.

11. A method according to claim 9, wherein the molar ratio of the component (B) to the component (A) is within the range of $10^{-1}:1$ to 10:1.

12. A method according to claim 9, wherein the molar ratio of the component (E) to the component (A) is within the range of $10^{-2}:1$ to $10^3:1$.

13. A method according to claim 9, wherein the inorganic halide is select-d from the group consisting of cesium chloride, sodium bromide, potassium bromide, rubidium bromide, cesium bromide an barium bromide.

14. A method according to claim 9, wherein the reaction pressure is within the range of 1 to 250 $Kg/cm^2$.

15. A method according to claim 9, wherein the reaction temperature is within the range of 60° to 250° C.

* * * * *